US00PP09551P

United States Patent [19]

Trees

[11] Patent Number: Plant 9,551

[45] Date of Patent: May 14, 1996

[54] GERANIUM PLANT NAMED 'BFP-788 BRIGHT SCARLET'

[75] Inventor: Scott C. Trees, Arroyo Grande, Calif.

[73] Assignee: Geo. J. Ball, Inc., West Chicago, Ill.

[21] Appl. No.: 431,423

[22] Filed: May 1, 1995

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Burns, Doane, Swecker & Mathis

[57] ABSTRACT

5The new and distinct *Pelargonium×hortorum* cultivar named 'BFP-788 Bright Scarlet' is provided. This new Zonal Geranium was the result of a controlled breeding program wherein a plant designated 1908-47 (non-patented in the United States) was pollinated by a plant designated PAS 231-1-2 (non-patented in the United States). The new cultivar forms attractive semi-double scarlet red florets. Medium green foliage is well retained during shipment. The growth habit is medium self-branching and does not require the use of a growth regulator.

1 Drawing Sheet

SUMMARY OF THE INVENTION

The present invention comprises a new and distinct Geranium cultivar, botanically known as *Pelargonium×hortorum* Bailey, and hereinafter is referred to by the cultivar name 'BFP-788 Bright Scarlet'.

The new cultivar is a product of a planned breeding program which had the objective of the creation of a Geranium cultivar that exhibits uniform flowers, medium green foliage, a medium self-branching growth habit that requires no growth regulator, a propensity for rapid rooting, and stable foliage coloration during shipment.

The breeding program that resulted in the production of the new cultivar of the present invention was carried out in a controlled environment during 1992 at Arroyo Grande, Calif., U.S.A. The female parent (i.e., seed parent) was a plant designated 1908-47 (non-patented in the United States) which exhibits single scarlet florets with dark green foliage. The male parent (i.e., pollen parent) was a plant designated PAS 231-1-2 (non-patented in the United States) which exhibits semi-double dark red florets with medium green foliage. The parentage of the new 'BFP-788 Bright Scarlet' cultivar can be summarized as follows:

1908-47×PAS 231-1-2.

'BEP-788 Bright Scarlet' was discovered and selected during 1992 as a highly distinctive flowering plant from among the progeny of the stated cross at Arroyo Grande, Calif., U.S.A. This plant was initially designated BFP-788.

It was found that the new cultivar of the present invention:

(a) exhibits attractive semi-double scarlet red florets, (b) forms attractive medium green foliage, and (c) exhibits a medium self-branching growth habit in the absence of a growth regulator.

When the plant material of the 'BEP-788 Bright Scarlet' cultivar is subjected to standard random amplified polymorphic DNA marker analysis (RAPD) using polymerase chain reaction (PCR) and a known set of DNA primers, it is found to exhibit a distinctive fingerprint map which is on file at the Ball FloraPlant Division of Geo. J. Ball, Inc. at Arroyo Grande, Calif., U.S.A.

The first act of asexual reproduction of 'BFP-788 Bright Scarlet' cultivar was accomplished when vegetative cuttings were taken from the initial selection in a controlled environment at Arroyo Grande, Calif., U.S.A., by a technician working under the direction and supervision of the originator of the new cultivar. Horticultural examination of plants resulting from such asexual propagation during 1993 has demonstrated that the combination of unique characteristics as herein described for the 'BFP-788 Bright Scarlet' cultivar is fixed and is retained through successive generations of such asexual reproduction.

The new 'BFP-788 Bright Scarlet' cultivar has not been observed under all possible environmental conditions. Accordingly, the described phenotype may vary somewhat with variations in the environment, such as temperature, light intensity, and day length.

Of the many commercial cultivars, the 'Alex' cultivar (U.S. Plant Pat. No. 5,311) is considered to be the most similar to the new cultivar of the present invention. Sometimes the 'Alex' cultivar is known as the 'Kim' cultivar. When the new cultivar of the present invention is compared to the 'Alex' cultivar, it is found that the 'BFP-788 Bright Scarlet' cultivar exhibits larger florets (e.g., approximately 4.4 to 5.2 cm. vs. approximately 4.3 to 4.6 cm.), longer internodes (e.g., approximately 2.0 to 3.0 cm. vs. approximately 1.5 to 2.0 cm.), and slightly smaller leaves (e.g., approximately 8.5 to 9.1 cm.×approximately 7.0 to 8.2 cm. vs. approximately 8.7 to 11.0 cm.×approximately 7.3 to 9.0 cm.).

The new cultivar of the present invention is being marketed by Geo. J. Ball, Inc. under the Designer trademark.

BRIEF DESCRIPTION OF THE PHOTOGRAPHS

The accompanying photographs show the new 'BFP-788 Bright Scarlet' cultivar with colors being as nearly true as it is reasonably possible to make the same in color illustrations of this character. The plant was being grown in a greenhouse at West Chicago, Ill., U.S.A.

DETAILED DESCRIPTION

Figure 1:
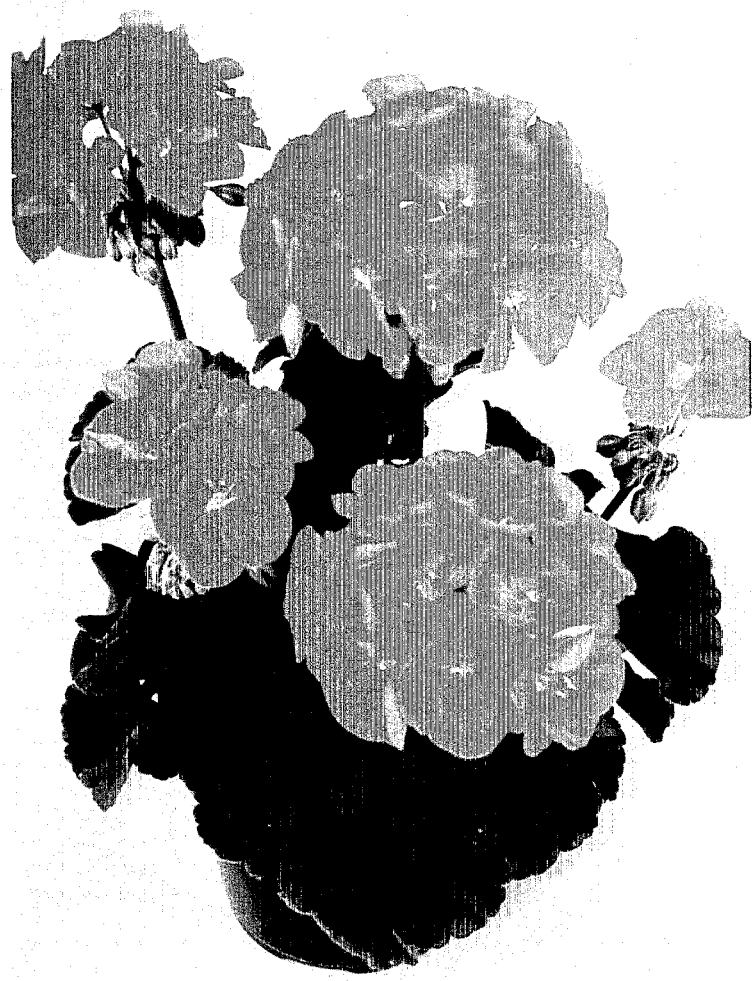
FIG. 1 illustrates the general appearance of the overall plant wherein the flower and foliage characteristics are illustrated.
Figure 2:
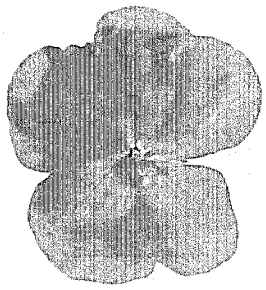
FIG. 2 illustrates the general appearance of a typical floret. The bloom coloration is considered to be slightly more accurately depicted in FIG. 2 than in FIG. 1.

The following observations, measurements and comparisons describe plants grown in Ball FloraPlant's greenhouses located at West Chicago, Ill., U.S.A., under conditions which approximate those generally used in commercial practice. In the following description, color references are made to the R.H.S. Colour Chart of The Royal Horticultural Society, London, England. The color values were determined between 11:00 and 11:45 a.m. on Jan. 3, 1995,under natural light conditions of 2,000 footcandles.

Classification:

*Botanical.—Pelargonium×hortorum* Bailey, cv. 'BFP-788 Bright Scarlet'.

*Commercial.*—Zonal Geranium.

Inflorescence

A. Umbel:

*Average diameter.*—Approximately 10.0 to 12.0 cm. compared to approximately 9.0 to 11.5 cm. for the 'Alex' cultivar.

*Average depth.*—Approximately 7.0 to 10.0 cm. compared to approximately 7.5 to 9.0. cm. for the 'Alex' cultivar.

*Peduncle length.*—Approximately 16.0 to 21.0 cm. compared to approximately 1.50 to 23.0 cm. for the 'Alex' cultivar.

*Pedicle length.*—Approximately 2.5 to 3.9 cm. compared to approximately 2.6 to 3.6 cm. for the 'Alex' cultivar.

*Number of umbels/plant.*—When grown in a 10 cm. pot at 9 weeks after the sticking of a rooted cutting, there commonly are approximately 4 to 6 umbels per plant. The 'Alex' cultivar also commonly forms approximately 4 to 6 umbels per plant.

*Number of florets/umbels.*—When grown in 10 cm. pots at 9 weeks, approximately 23 to 35 florets per umbel commonly are formed. This compares to approximately 20 to 34 florets per umbel for the 'Alex' cultivar under the same growing conditions.

B. Corolla:

*Average diameter.*—Approximately 4.4 to 5.2 cm. compared to approximately 4.3 to 4.6 cm. for the 'Alex' cultivar.

*Form.*—Both the 'BFP-788 Bright Scarlet' cultivar and the 'Alex' cultivar are semi-double with petaloids. Both the 'BFP-788 Bright Scarlet' cultivar and the 'Alex' cultivar commonly possess approximately 5 to 6 petals per floret.

*Number of petaloids.*—Commonly forms 1 to 3 petaloids per floret whereas the 'Alex' cultivar commonly forms 1 to 2 petaloids per floret.

*Color.*—General tonality from a distance of three meters: scarlet. Adaxial: Red Group 44B. This compares to Red Group 40A with a spot of Red Group 53D on the upper two petals for the 'Alex' cultivar. Abaxial: Red Group 41A. This compares to Red Group 40B for the 'Alex' cultivar.

C. Bud:

*Shape.*—Oval-rounded.

*Color.*—Adaxial: Red Group 44B compared to Red Group 40A for the 'Alex' cultivar. Abaxial: Red Group 41A compared to Red Group 40B for the 'Alex' cultivar.

D. Reproductive organs:

*Androecium.*—The anthers are commonly approximately 1.5 to 2.0 mm. in length. The pollen color is Orange-Red Group 31A for both the 'BFP-788 Bright Scarlet' cultivar and the 'Alex' cultivar. The filaments are approximately 11.0 mm. in length.

*Gynoecium.*—The pistil length commonly is approximately 9.0 mm. There is a single stigma which commonly has a length of approximately 3.0 mm. which commonly branches into 5 parts, and the style length is approximately 5.0 to 6.0 mm.

*Fertility.*—Can produce fruits.

E. Spring flowering response period: Approximately 6 to 7 weeks from rooted cuttings under greenhouse conditions.

F. Outdoor flower production: Freely flowering under outdoor growing conditions with subtantially continuous blooming.

G. Durability: Ships well.

Plant

A. Foliage: Medium green (as illustrated).

*Form.*—Reniform, with cordate base.

*Margin.—Crenate.*

*Color.*—Adaxial: Yellow-Green Group 147B. This compares to Yellow-Green Group 147A for the 'Alex' cultivar. Abaxial: Green Group 137A for both the 'BFP-788 Bright Scarlet' cultivar and the 'Alex' cultivar.

*Size.*—Approximately 8.5 to 9.1 cm. at the widest point and approximately 7.0 to 8.2 cm. at the narrowest point. This compares to approximately 8.7 to 11.0 cm. at the widest point and approximately 7.3 to 9.0 cm. at the narrowest point for the 'Alex' cultivar.

*Tolerance to Botrytis.*—Some in the field.

B. General appearance and form:

*Internode length.*—Commonly varies from approximately 2.0 to 3.0 cm. This compares to approximately 1.5 to 2.0 cm. for the 'Alex' cultivar.

*Branching pattern.*—Freely basal branching. No pinching is required to obtain self-branching. A medium self-branching growth habit is observed in the absence of a growth regulator.

*Height.*—Approximately 28 to 32 cm. above a 10 cm. pot at 9 weeks under standard greenhouse conditions. This compares to approximately 25 to 34 cm. for the 'Alex' cultivar.

I claim:

1. A new and distinct Geranium plant named 'BFP-788 Bright Scarlet' substantiually as herein shown and described which:

(a) exhibits attractive semi-double scarlet red florets, (b) forms attractive medium green foliage, and (c) exhibits a medium self-branching growth habit in the absence of the use of a growth regulator.

* * * * *